US012033317B2

(12) United States Patent
Zheng et al.

(10) Patent No.: US 12,033,317 B2
(45) Date of Patent: Jul. 9, 2024

(54) WATER FLOSSER WITH IMAGE SYSTEM

(71) Applicant: Xiamen Solex High-Tech Industries Co., Ltd., Xiamen (CN)

(72) Inventors: Jie Zheng, Xiamen (CN); Weisi Lin, Xiamen (CN); Cen Yang, Xiamen (CN); Guihua Yan, Xiamen (CN)

(73) Assignee: Xiamen Solex High-Tech Industries Co., Ltd., Xiamen (CN)

( * ) Notice: Subject to any disclaimer, the term of this patent is extended or adjusted under 35 U.S.C. 154(b) by 807 days.

(21) Appl. No.: 17/166,645

(22) Filed: Feb. 3, 2021

(65) Prior Publication Data
US 2022/0036543 A1     Feb. 3, 2022

(30) Foreign Application Priority Data

Jul. 31, 2020   (CN) .......................... 202010761636.3
Oct. 17, 2020   (CN) .......................... 202011113302.1

(51) Int. Cl.
G06T 7/00      (2017.01)
A61C 17/02     (2006.01)
A61C 17/028    (2006.01)

(52) U.S. Cl.
CPC ........ G06T 7/0012 (2013.01); A61C 17/0202 (2013.01); A61C 17/028 (2013.01); *G06T 2207/30036* (2013.01)

(58) Field of Classification Search
CPC ......... G06T 7/0012; G06T 2207/30036; A61C 17/0202; A61C 17/028
See application file for complete search history.

(56) References Cited

U.S. PATENT DOCUMENTS

| 2008/0008979 | A1  |   | 1/2008 | Thomas et al. |
| 2017/0100223 | A1* | 4/2017 | Silverberg ........... A46B 5/0095 |
| 2021/0085436 | A1* | 3/2021 | Evans ................ A61C 17/0202 |
| 2023/0200958 | A1* | 6/2023 | Garrigues .......... A61C 17/0202 |
| | | | | 433/80 |

FOREIGN PATENT DOCUMENTS

| DE | 10043749 A1   | 3/2002 |
| JP | H05-111497 A  | 5/1993 |
| JP | 2001-212161 A | 8/2001 |
| JP | 2013-000383 A | 1/2013 |
| JP | 2019-517838 A | 6/2019 |

OTHER PUBLICATIONS

Corresponding Japanese Patent Application No. 2021-071419, Search Report dated May 31, 2022.
Corresponding Japanese Patent Application No. 2021-071419, First Office Action dated Jun. 7, 2022.

* cited by examiner

Primary Examiner — Steven O Douglas
(74) Attorney, Agent, or Firm — Cooper Legal Group LLC

(57) ABSTRACT

A water flosser with an image system comprises a body, a water outlet spout, and an image system. The water outlet spout and a camera lens of the image system are disposed on the body, and an area covered by ejected water ejected from the water outlet spout at least partially coincides with an image area of the image system.

19 Claims, 22 Drawing Sheets

WATER FLOSSER WITH IMAGE SYSTEM

RELATED APPLICATIONS

This application claims priority to Chinese patent application number 202010761636.3, filed Jul. 31, 2020, and Chinese patent application number 202011113302.1, filed Oct. 17, 2020. Chinese patent application number 202010761636.3 and Chinese patent application number 202011113302.1 are incorporated herein by reference.

FIELD OF THE DISCLOSURE

The present disclosure relates to a personal care product, and in particular relates to an oral care product.

BACKGROUND OF THE DISCLOSURE

A water flosser is a personal care product in the field of oral health care. Water in a water tank is pumped into a water outlet spout by a water pump to form a jet to flush a mouth and teeth of a user. Compared with ordinary toothbrushes, the water flosser has reduced oral diseases including gingivitis, periodontal disease, and gum bleeding more scientifically and effectively because of the ability of the water flosser to remove dental plaque more thoroughly, and the water flosser has gradually attracted the interest of consumers.

When cleaning an oral cavity, it is sometimes necessary to observe common dental problems in the oral cavity, including crowded teeth, loose teeth, whistling teeth, fallen teeth, and buck teeth. At the same time, unclean teeth and foreign bodies can easily cause tooth decay and periodontal disease. However, the existing electric toothbrushes and water flossers can only clean the teeth and cannot check oral conditions, observe the oral conditions, and remove foreign bodies. Therefore, the existing electric toothbrushes and water flossers cannot help users understand the oral conditions and increases a risk of dental disease.

BRIEF SUMMARY OF THE DISCLOSURE

In order to solve the technical problems, the present disclosure provides a water flosser with an image system. An image area of the image system is consistent with a washing area of a water outlet spout, and a flushing effect is more intuitive.

In order to solve the technical problems, a technique solution of the present disclosure is as follows.

A water flosser with an image system comprises a body, a water outlet spout, and an image system. The water outlet spout and a camera lens of the image system are disposed on the body, and an area covered by ejected water ejected from the water outlet spout at least partially coincides with an image area of the image system.

In a preferred embodiment, an image processing portion of the image system is disposed in the body.

In a preferred embodiment, a connection position between the image system and the body is disposed on a side of the water outlet spout facing the ejected water.

In a preferred embodiment, a lens surface of the image system is lower than a water outlet surface of the water outlet spout.

In a preferred embodiment, a connection position between the image system and the body is disposed on a side of the water outlet spout opposite to the ejected water.

In a preferred embodiment, a lens surface of the image system is higher than a water outlet surface of the water outlet spout.

In a preferred embodiment, a lens surface of the image system is disposed on a side of a water outlet opening of the water outlet spout.

In a preferred embodiment, the image system is disposed in a water outlet opening of the water outlet spout.

In a preferred embodiment, the area covered by the ejected water ejected from the water outlet spout always appears in the image area of the image system.

In a preferred embodiment, the water outlet spout and the camera lens are respectively detachably connected to the body.

In a preferred embodiment, the camera lens and the body define a non-detachable connection.

In a preferred embodiment, the body comprises a cavity for accommodating the camera lens and the water outlet spout.

In a preferred embodiment, the body comprises a water tank, and a bottom portion of the body comprises a cover configured to open or close the water tank.

In a preferred embodiment, one or more control switches are disposed on the body.

In a preferred embodiment, the one or more control switches comprise at least one switch configured to control the water outlet spout to discharge water or to stop discharging water, or the one or more control switches are configured to control the image system to be switched on or to be switched off.

In a preferred embodiment, a water flosser control switch of the one or more control switches and a lighting switch of the one or more control switches are independent from each other.

In a preferred embodiment, the one or more control switches comprise an image switch. After the image system is switched on, the image switch is pressed to photograph a current image area of the image system In a preferred embodiment, a water flosser control switch of the one or more control switches is repeatedly pressed to change a water outlet gear position of the water outlet spout.

In a preferred embodiment, an application disposed on a smart terminal. A wireless connection is defined between the application and the image system, and the image area of the image system is displayed on the application in real time or photos of an oral cavity taken by the image system are displayed on the application.

Compared with the existing techniques, the technical solution has the following advantages.

1. The water flosser of the present disclosure is specially designed with the relative position of the water flosser and the image system in mind, so that the imaging position of the image system is consistent with (i.e., aligned with) the flushing position of the water flosser. Therefore, when the user observes certain oral cavity positions need to be flushed through the image system, the switch is just pressed to flush the positions. There is no need to adjust the positions, and the flushing effect can be observed in real time through the image system, which is very clear and intuitive.

2. In the water flosser of the present disclosure, the image system and the water flosser can be used separately, which is convenient for the user to directly clean the oral cavity or directly observe the oral cavity.

DETAILED DESCRIPTION OF THE EMBODIMENTS

Technique solutions of embodiments of the present disclosure will be definitely and completely described below in combination with the accompanying drawings of embodiments of the present disclosure. The following embodiments are merely some embodiments of the present disclosure and are not all embodiments of the present disclosure. Thus, it is intended that the present disclosure cover all embodiments provided that they are made without creative work by those skilled in the art based on the embodiments of the present disclosure.

Hereinafter, the terms "upper", "lower", "inner", "outer", "top", "bottom", and other directional terms used to refer to directions and positions should be understood to refer to the directions and the positions of the drawings. The terms do not indicate that the device and the element should be defined or operated in a certain direction and have a certain direction, but are intended to enable the present disclosure to be clearly understood and to simplify the description. Therefore, the present disclosure is not limited thereto. Further, the terms "first", "second", etc. used in the present disclosure do not indicate relative importance in the present disclosure, but are intended to distinguish one part from other parts.

Hereinafter, unless otherwise specified and limited, the terms "assemble", "dispose", "encompass", "connect", etc., should be broadly interpreted. For example, "connect" can be understood to refer to a fixed connection, a detachable connection, an integral connection, a mechanical connection, or an electrical connection, a direct connection, an indirect connection through an intermediate member, or a commutation between inner sides of two components. The terms described in the present disclosure follow a specific definition of the present disclosure understood by those skilled in the art.

Embodiment 1

Figure 1:
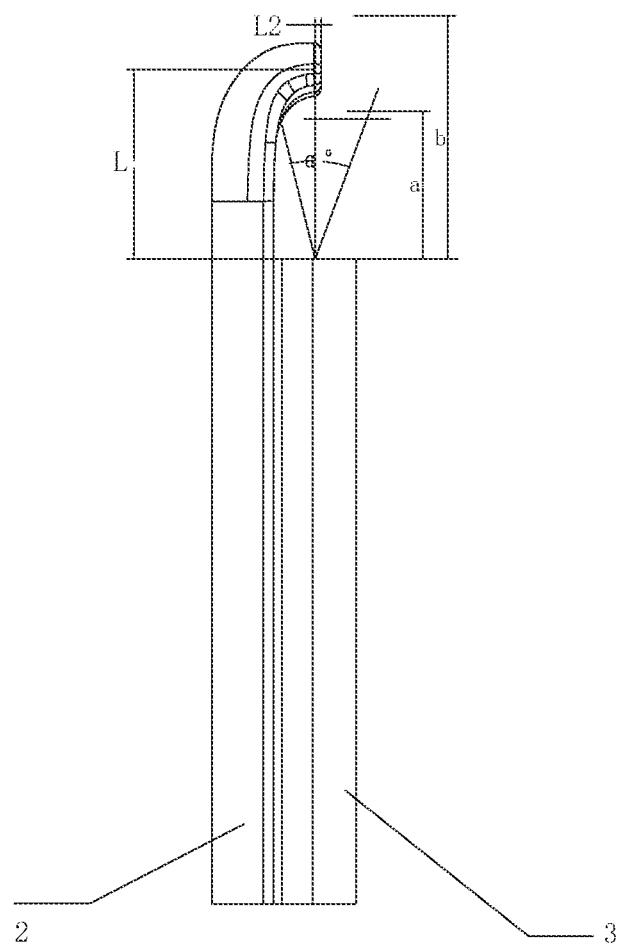
FIG. 1 illustrates a side view of a water flosser of Embodiment 1 of the present disclosure.
Figure 2:
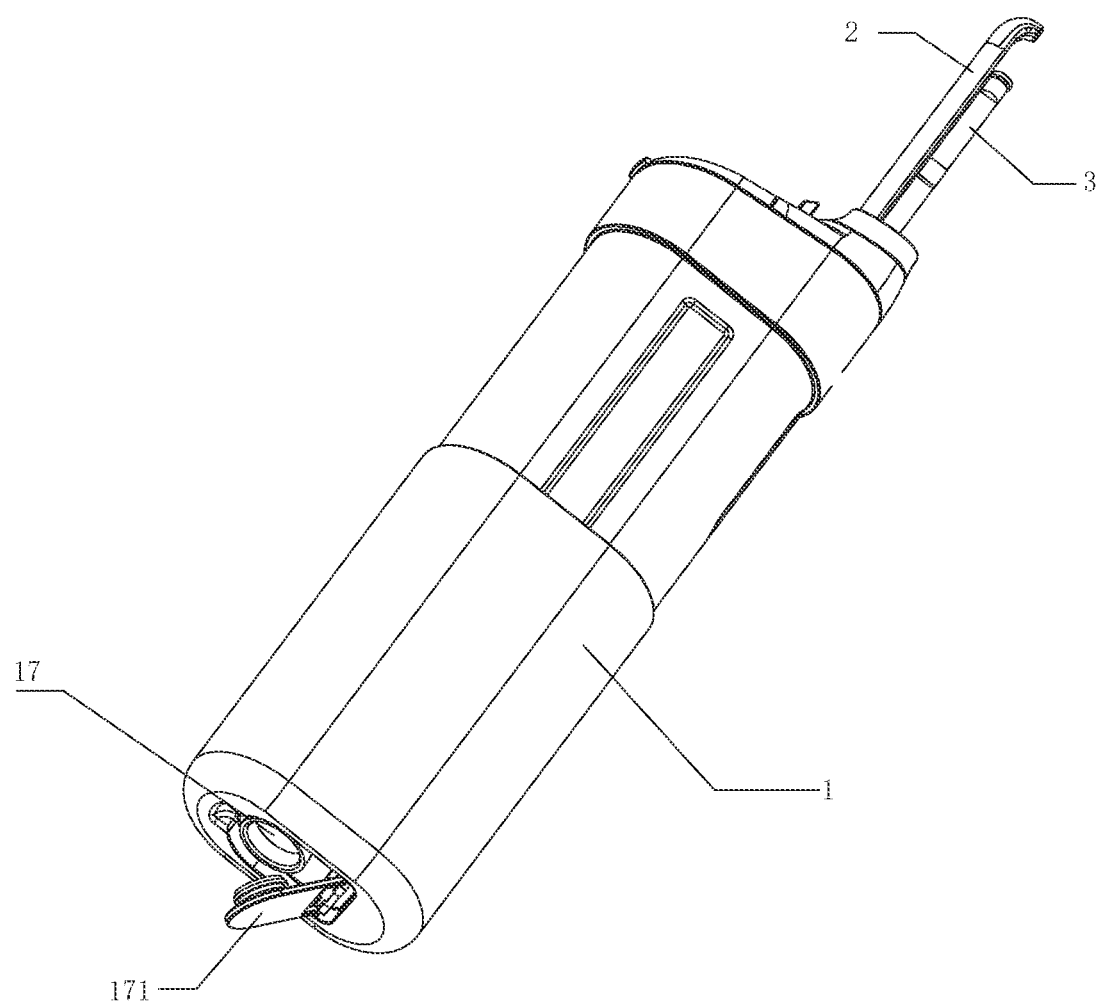
FIG. 2 illustrates a perspective view of the water flosser of Embodiment 1 of the present disclosure.
Figure 3:
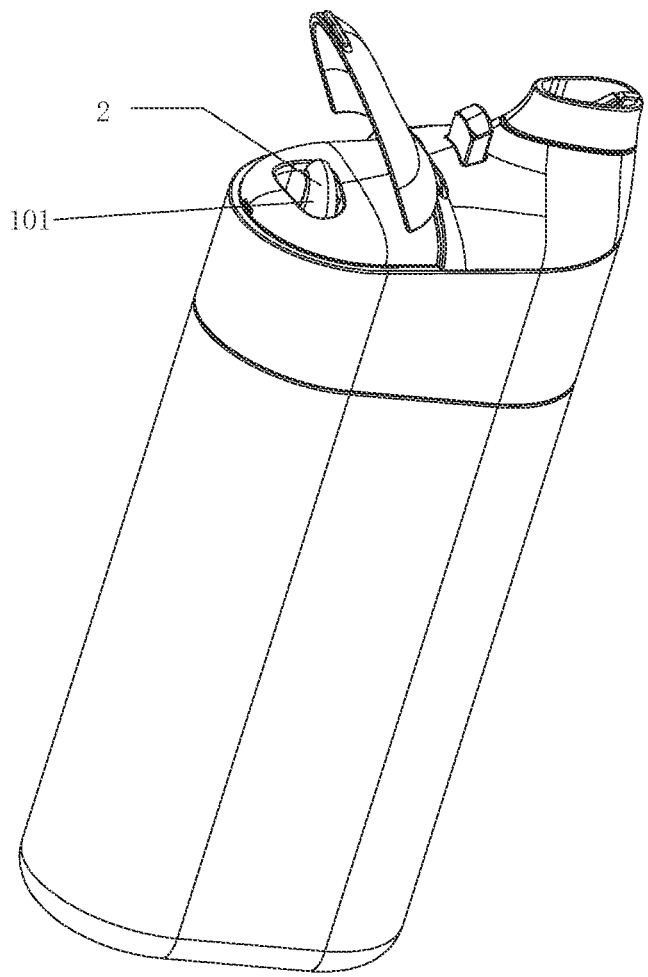
FIG. 3 illustrates a perspective view of the water flosser of Embodiment 1 of the present disclosure in a storage state.

Referring to FIGS. 1-3, a water flosser with an image system comprises a body 1, a water outlet spout 2, and an image system 30. A camera lens 3 of the image system 30 is disposed on the body 1 and is positioned on a side of the water outlet spout 2 facing where ejected water is ejected from the water outlet spout 2. An image processing portion of the image system 30 is disposed in the body 1. The camera lens 3 can be an endoscope or an infrared thermal imaging camera lens.

A focal length of the camera lens 3 ranges from a to b. The values of a and b are different for different camera lenses. A lens surface of the camera lens 3 is lower than a water outlet opening (i.e., a water outlet surface or a water outlet hole) of the water outlet spout 2, and the lens surface of the camera lens 3 faces the water outlet spout 2. The water outlet opening of the water outlet spout 2 is positioned in an image area of the camera lens 3.

The image area of the camera lens 3 partially coincides with a washing area of the water outlet spout 2 (i.e., an area covered by ejected water ejected from the water outlet spout 2) due to the aforementioned structure, and the washing area of the water outlet spout 2 always appears in the image area of the camera lens 3. In some embodiments, the water outlet spout 2 and the washing area of the water outlet spout 2 always appear in the image area of the camera lens 3. In this way, when the user observes a certain part of an oral cavity that needs to be washed using the camera lens 3, the washing area and the water outlet spout 2 can be observed from the image area of the camera lens 3, and this part of the oral cavity can be washed merely by pressing a switch (e.g., a water flosser control switch 11). There is no need to adjust a position of the water outlet spout 2, a washing effect can be observed in real time using the camera lens 3, and an operation is very clear and intuitive.

In this embodiment, a height difference L between the lens surface of the camera lens 3 and the water outlet opening of the water outlet spout 2 satisfies: a<L<b. A distance L2 between the water outlet opening of the water outlet spout 2 and a central axis of the camera lens 3 satisfies: $0 \leq L2 \leq \tan(\alpha/2)*L$. α represents a dispersion angle of the camera lens 3.

In this embodiment, in order to facilitate the user storing the water outlet spout 2 and the camera lens 3, the water outlet spout 2 and the camera lens 3 are respectively detachably connected to the body 1. The water outlet spout 2 is directly disposed in the body 1. A bottom portion of the camera lens 3 is disposed with a connector 300, the connector 300 enables the bottom portion of the camera lens 3 to be connected to a bottom portion of the body 1 by a mechanical connection and an electrical connection, so that the camera lens 3 obtains electric power from the body 1 and is secured to the body 1. The connector 300 can comprise a magnet and an electrically conductive elastic sheet 31, which are existing techniques and will not be further described here. As a simple replacement of this embodiment, the camera lens 3 can also be secured to the body 1 that prevents the camera lens 3 from being detached from the body 1.

In this embodiment, in order to facilitate the user storing the water outlet spout 2 and the camera lens 3 after the water outlet spout 2 and the camera lens 3 have been detached from the body 1, the body 1 comprises a cavity 101 for accommodating the camera lens 3 and the water outlet spout 2. In this way, the user does not need to prepare an additional storage box, and it is very convenient to carry when traveling.

In addition, the water flosser of this embodiment is a portable water flosser. Therefore, the body 1 comprises a built-in water tank 17, and the bottom portion of the body 1 comprises a cover 171 configured to open or close the built-in water tank 17. In this way, all required basic components can be integrated on the body 1 and a storage volume is small, which is further convenient to carry for the users.

Figure 10:
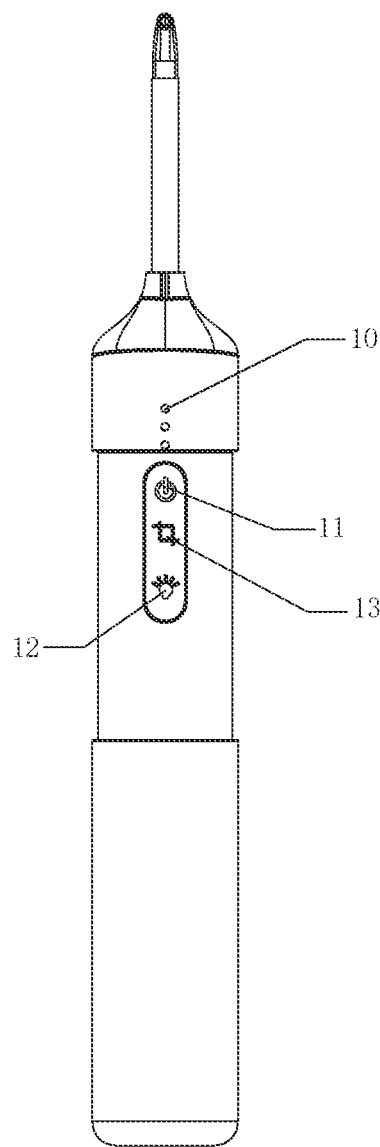
FIG. 10 illustrates a front view of the water flosser of Embodiment 1 of the present disclosure.

In addition, referring to FIG. 10, the body 1 is disposed with one or more control switches comprising the water flosser control switch 11, a lighting switch 12, and an image switch 13. As a simple replacement of this embodiment, the one or more control switches can also be a push switch, and the push switch can be pushed to different positions to achieve operations comprising controlling the water outlet spout 2 to discharge water and to stop discharging water or switching on or off the camera lens 3.

When the user uses the water flosser, the water flosser control switch 11 of the water flosser is pressed to control the water outlet spout 2 to discharge water or to stop discharging water, and the lighting switch 12 is pressed to control the camera lens 3 to be switched on or to be switched off. After the camera lens 3 is switched on, the image switch 13 is pressed to photograph a current image area of the camera lens 3.

In order to facilitate the user using the water flosser or the camera lens 3 alone, the water flosser control switch 11 and the lighting switch 12 are independent from each other. There is no dependency between the water flosser control switch 11 and the lighting switch 12. The user can switch on a corresponding function of the switch by pressing any one of the one or more control switches. Therefore, it is convenient for the user to directly clean the oral cavity or directly observe the oral cavity.

In addition, the user can also repeatedly press the water flosser control switch 11 to change water outlet gearing positions of the water outlet spout 2 to choose one's own suitable washing force. In order to allow the user to intuitively know a current washing gear position, the body 1 is also disposed with one or more indicator lights 10 for indicating the current water outlet gear position. The number of indicator lights 10 is consistent with the number of washing gear positions. When the number of washing gear positions increases or decreases, the number of indicator lights 10 increases or decreases accordingly.

In order to facilitate the user observing one's own oral cavity, the water flosser further comprises an application (APP) disposed on a smart terminal. The APP defines a wireless connection with the camera lens 3, and the image area of the camera lens 3 is displayed on the APP in real time or photos of the oral cavity taken by the camera lens 3 are displayed on the APP. In this way, the user can observe one's own oral cavity in real time while washing or can store the photos of one's oral cavity for careful observation.

Figure 4:
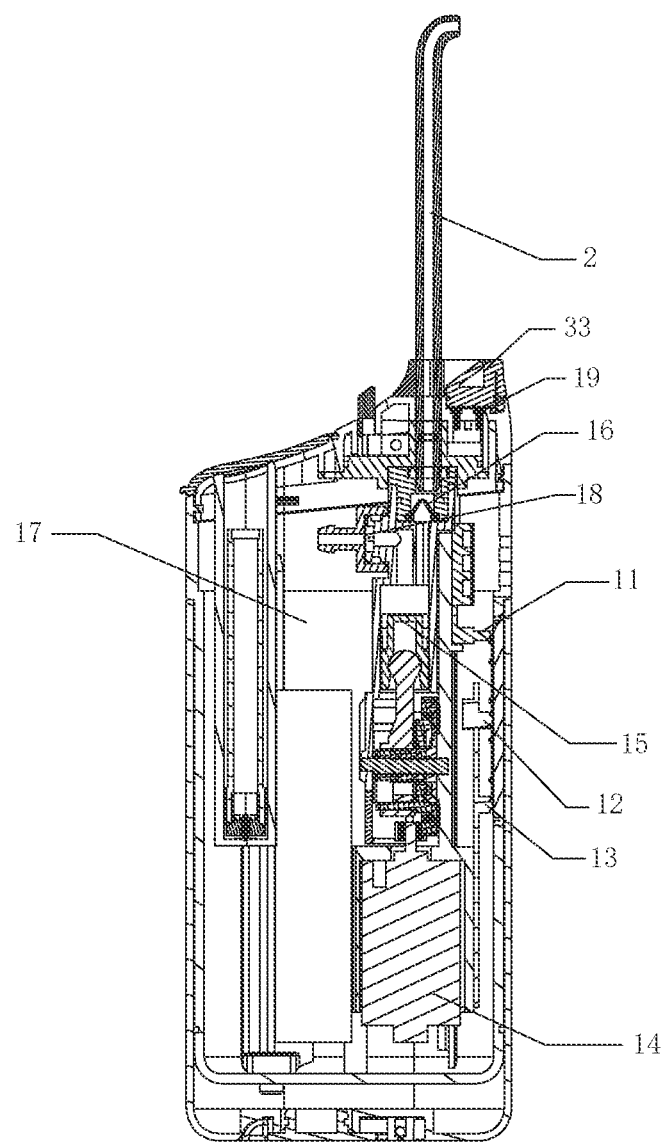
FIG. 4 illustrates a cross-sectional view of the water flosser of Embodiment 1 of the present disclosure when merely a water outlet spout is disposed on a body.
Figure 5:
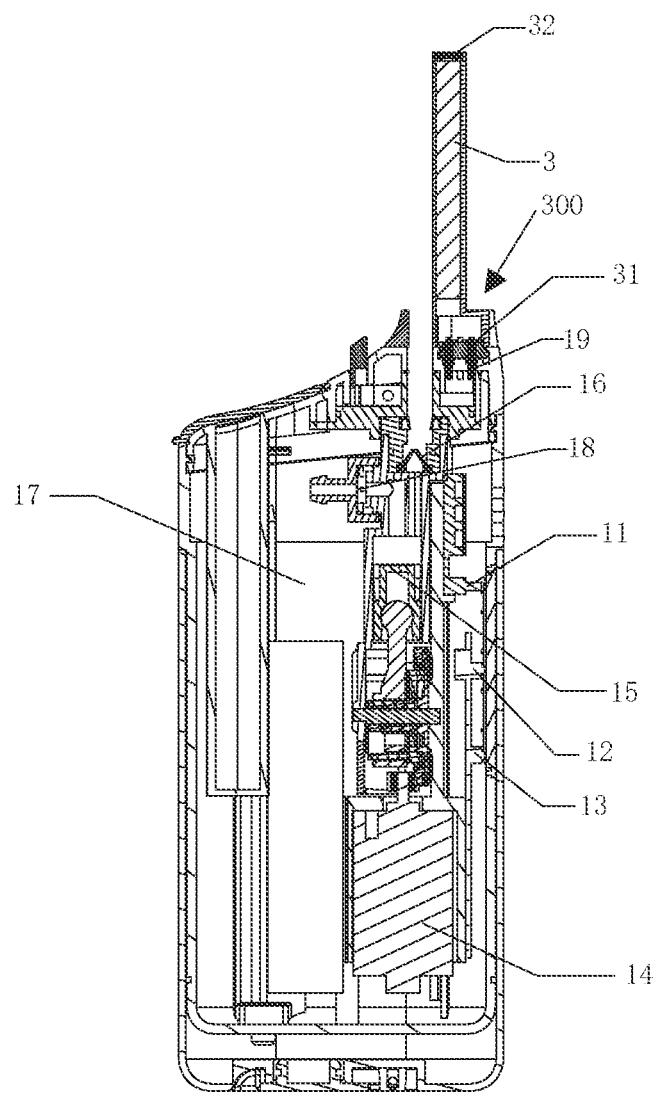
FIG. 5 illustrates a cross-sectional view of the water flosser of Embodiment 1 of the present disclosure when merely an image system is disposed on the body.

Referring to FIGS. 4 and 5, in order to achieve water discharging function, the body 1 is further disposed with a motor 14 configured to drive a piston assembly 15. The motor 14 drives the piston assembly 15 to reciprocate so as to enable water in the water tank 17 to be pumped into a pipe 151 disposed in the body 1. The pipe 151 is connected to the water outlet spout 2 through a duckbill valve 16 so as to prevent the water in the water outlet spout 2 from flowing back. The water tank 17 is connected to the pipe 151 through a check valve 18 so as to prevent the water in the pipe 151 from flowing back into the water tank 17.

In order to achieve an image function of the camera lens 3, the body 1 is further disposed with a circuit board of the camera lens 3 and an electrically conductive contact point 19 electrically connected to the electrically conductive elastic sheet 31 of the camera lens 3. The electrically conductive contact point 19 is connected to the circuit board through a wire. An end of the camera lens 3 facing the oral cavity is also disposed with a waterproof lens 32 configured to protect the camera lens 3. At the same time, when the camera lens 3 is not disposed on the body 1, a waterproof cover 33 is disposed on the body 1 to cover the electrically conductive contact point 19.

The lighting switch 12 and the image switch 13 are connected to the circuit board of the camera lens 3, and the water flosser control switch 11 is connected to a circuit board of the water flosser. The circuit board of the camera lens 3 and the circuit board of the water flosser are independent from each other to ensure that the camera lens 3 and the water flosser can be used separately without affecting each other.

Figure 6:
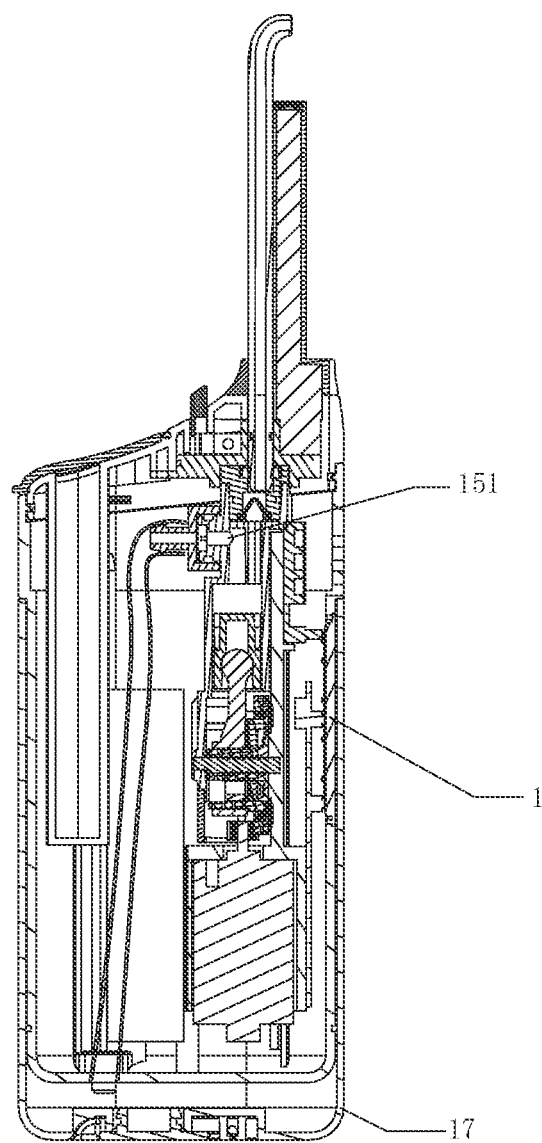
FIG. 6 illustrates a cross-sectional view of the water flosser of Embodiment 1 of the present disclosure when a water tank is in a contracted position.
Figure 7:
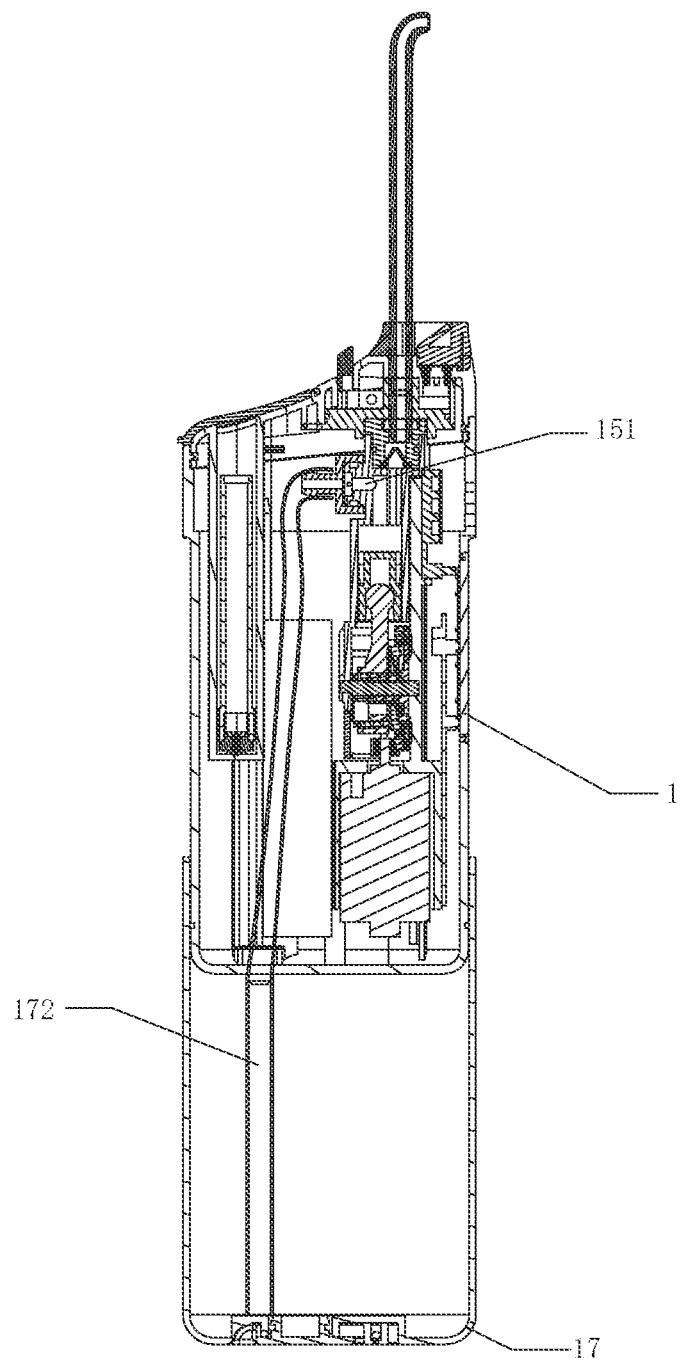
FIG. 7 illustrates a cross-sectional view of the water flosser of Embodiment 1 of the present disclosure when the water tank is in an extended position.

Referring to FIGS. 6 and 7, in this embodiment, an outer wall of the body 1 is further slidably connected to an inner wall of the water tank 17, so that the water tank 17 moves between an extended position and a contracted position. A telescopic tube 172 is disposed in the water tank 17, so that the water in the water tank 17 can be drawn by the piston assembly 15 disposed in the body 1. An upper end of the telescopic tube 172 is maintained in communication with the pipe 151 disposed in the body 1, and a lower end of the telescopic tube 172 extends or contracts corresponding to an extension or a contraction of the water tank 17. The water tank 17 is slidably connected to the body 1. The water tank 17 is configured to be slide to the contracted position to reduce a storage volume during a storage process, and the water tank 17 is configured to be slide to the extended position to increase an effective volume of the water tank 17 when in use.

Figure 8:
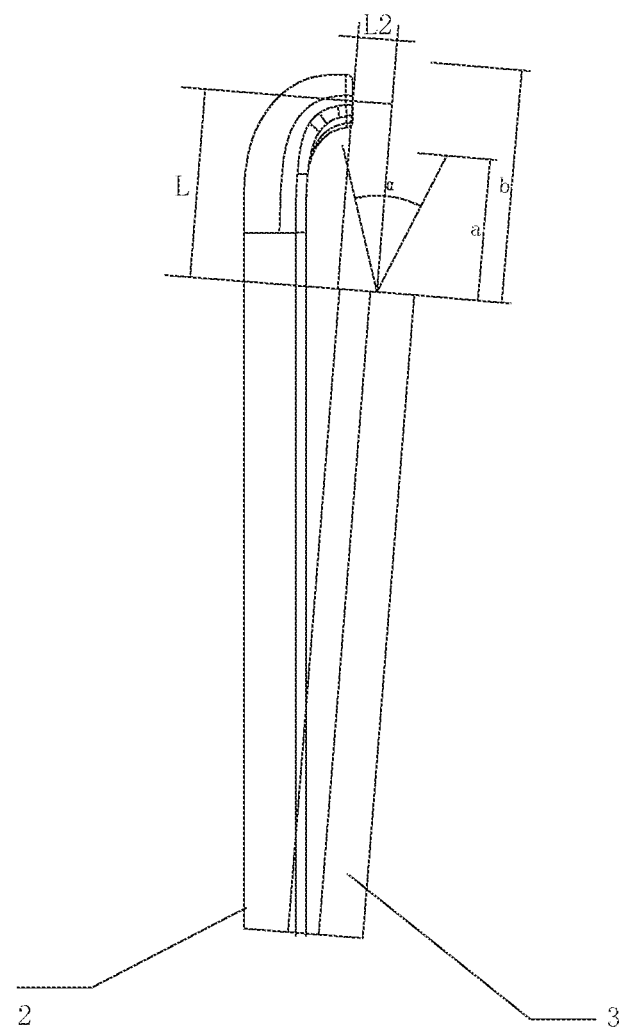
FIG. 8 illustrates a side view of the water flosser in another position between the image system and the water outlet spout of Embodiment 1 of the present disclosure.
Figure 9:
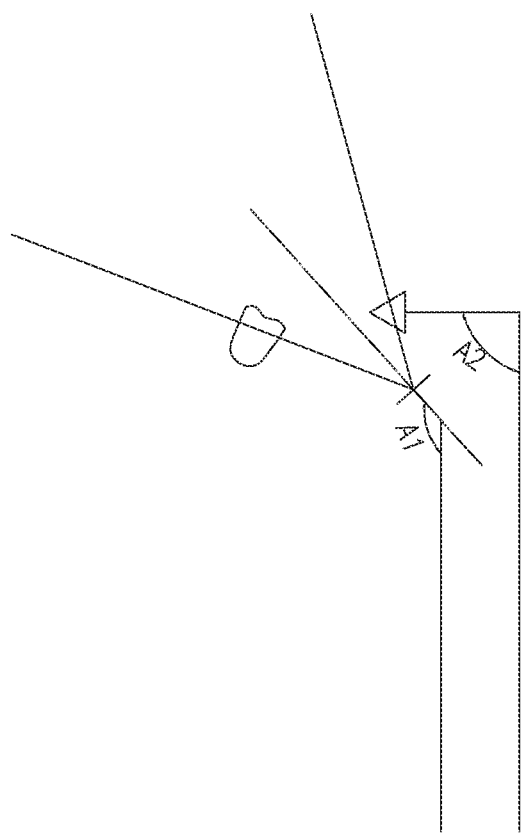
FIG. 9 illustrates a schematic view of an image area of the image system of Embodiment 1 of the present disclosure.

In this embodiment, for example, the central axis of the camera lens 3 is perpendicular to a central axis of the water outlet opening of the water outlet spout 2. In a practical design, the central axis of the camera lens 3 and the central axis of the water outlet opening of the water outlet spout 2 can also define an angle other than 90°, as long as the height difference L between the lens surface of the camera lens 3 and the water outlet opening of the water outlet spout 2 satisfies: a<L<b and, referring to FIG. 8, the distance L2 between the water outlet opening of the water outlet spout 2 and the central axis of the camera lens satisfies: $0 \leq L2 \leq \tan(\alpha/2)*L$.

Figure 11:
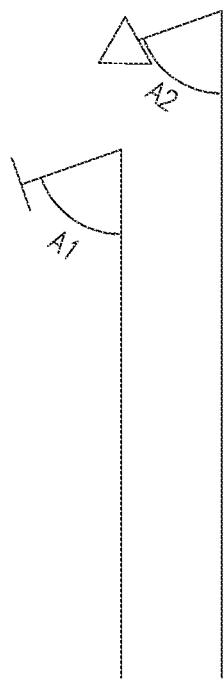
FIGS. 11-19 illustrate schematic views of various positions between an image angle and a water outlet angle of the water outlet spout of Embodiment 1 of the present disclosure.
Figure 12:
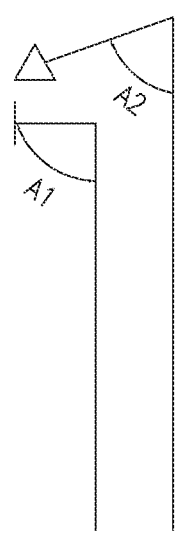
Figure 13:
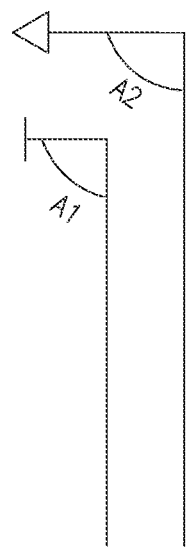
Figure 14:
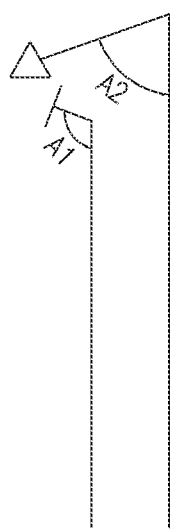
Figure 15:
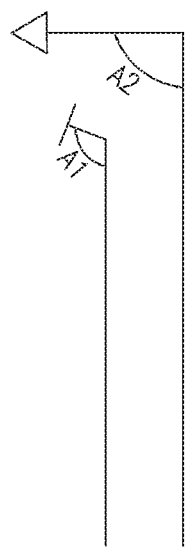
Figure 16:
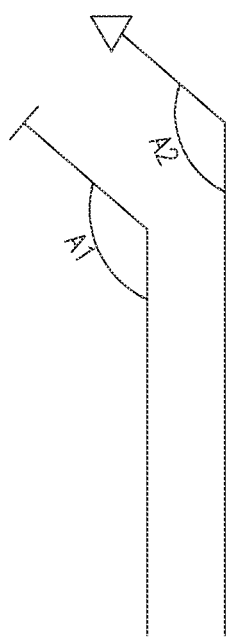
Figure 17:
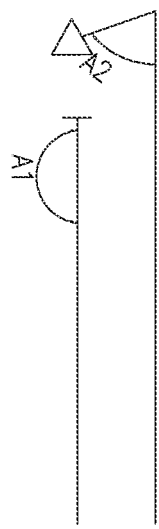
Figure 18:
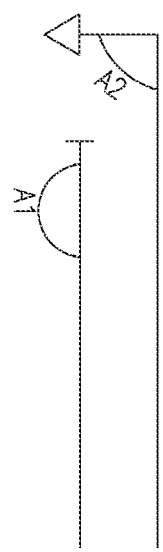
Figure 19:
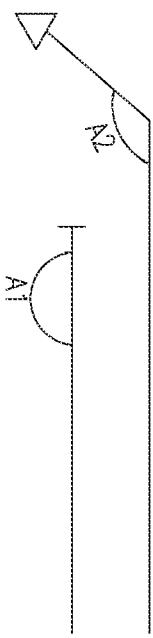

With respect to an image angle A1 of the camera lens 3 and a water discharging angle A2 of the water outlet spout 2, FIGS. 11-19 illustrate various positional relationships of the image angle A1 of the camera lens 3 and the water discharging angle A2 of the water outlet spout 2. Referring to FIGS. 11, A1 and A2 are respectively less than 90°. Referring to FIG. 12, A1 is equal to 90°, and A2 is less than 90°. Referring to FIGS. 13, A1 and A2 are respectively equal to 90°. Referring to FIG. 14, A1 is greater than 90°, and A2 is less than 90°. Referring to FIG. 15, A1 is greater than 90°, and A2 is equal to 90°. Referring to FIGS. 16, A1 and A2 are respectively greater than 90°. Referring to FIG. 17, A1 is equal to 180°, and A2 is less than 90°. Referring to FIG. 18, A1 is equal to 180°, and A2 is equal to 90°. Referring to FIG. 19, A1 is equal to 180°, and A2 is greater than 90°.

Embodiment 2

In Embodiment 1, a connection position between the camera lens 3 and the body 1 is positioned on a first side of the water outlet spout 2 facing the ejected water, and the lens surface of the camera lens 3 is lower than the water outlet opening of the water outlet spout 2. In this embodiment, a connection position of the camera lens 3 and the body 1 is on a second side of the water outlet spout 2 opposite to the ejected water, and the lens surface of the camera lens 3 is higher than the water outlet opening of the water outlet spout 2.

Figure 20:
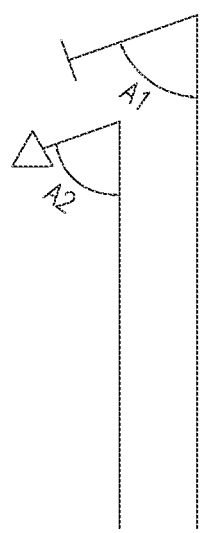
FIGS. 20-25 illustrate schematic views of various positions between an image angle and a water outlet angle of a water outlet spout of Embodiment 2 of the present disclosure.
Figure 21:
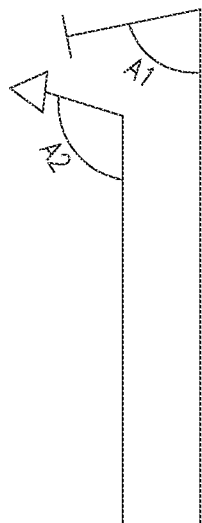
Figure 22:
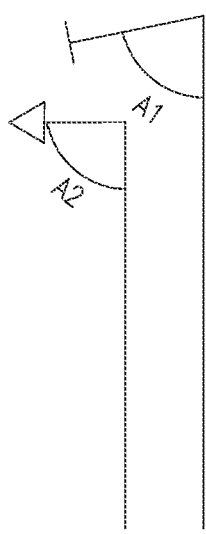
Figure 23:
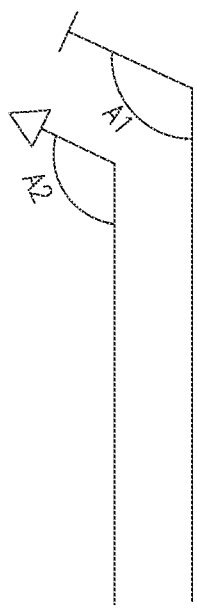
Figure 24:
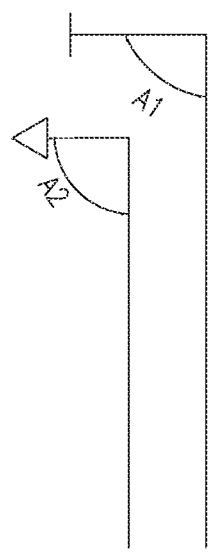
Figure 25:
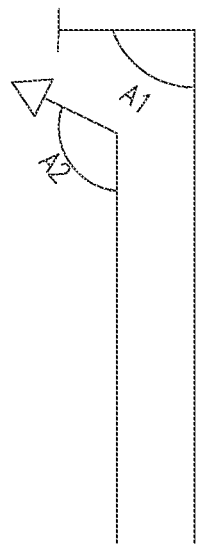

With respect to the image angle A1 of the camera lens 3 and a water discharging angle A2 of the water outlet spout 2, FIGS. 20-25 illustrate various positional relationships of the image angle A1 of the camera lens 3 and the water discharging angle A2 of the water outlet spout 2 of Embodiment 2. Referring to FIGS. 20, A1 and A2 are respectively less than 90°. Referring to FIG. 21, A1 is less than 90°, and A2 is greater than 90°. Referring to FIG. 22, A1 is less than 90°, and A2 is equal to 90°. Referring to FIG. 23, A1 and A2 are respectively greater than 90°. Referring to FIGS. 24, A1 and A2 are respectively equal to 90°. Referring to FIG. 25, A1 is equal to 90°, and A2 is greater than 90°.

Embodiment 3

Figure 26:
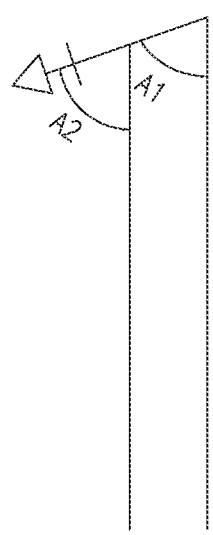
FIGS. 26-34 illustrate schematic views of various positions between an image angle and a water outlet angle of a water outlet spout of Embodiment 3 of the present disclosure.
Figure 27:
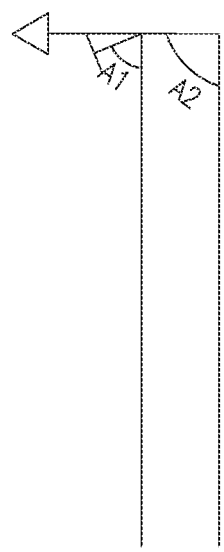
Figure 28:
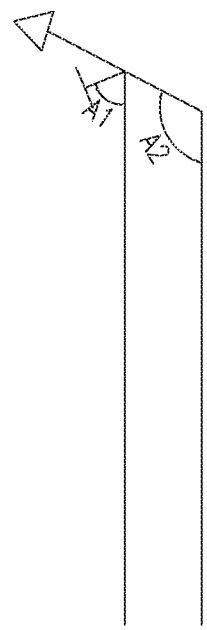
Figure 29:
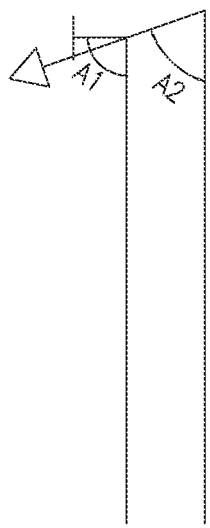
Figure 30:
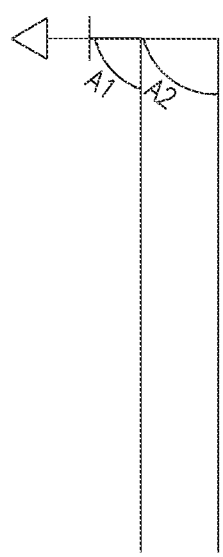
Figure 31:
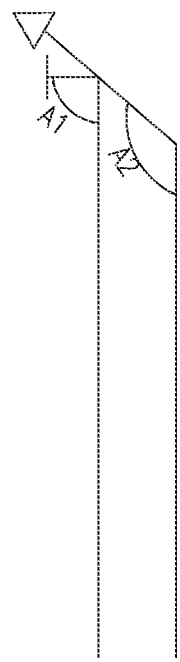
Figure 32:
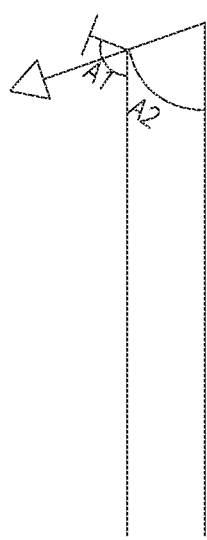
Figure 33:
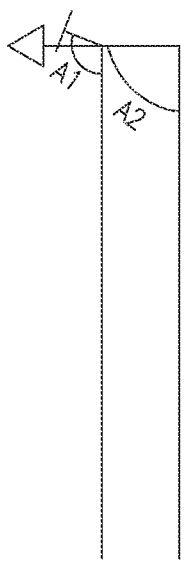
Figure 34:
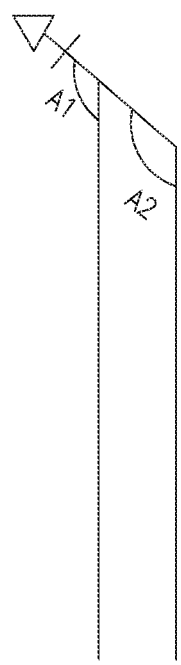

In this embodiment, the lens surface of the camera lens 3 is positioned on a side of the water outlet opening of the water outlet spout 2. With respect to the image angle A1 of the camera lens 3 and a water discharging angle A2 of the water outlet spout 2, FIGS. 26-34 illustrate various positional relationships of the image angle A1 of the camera lens 3 and the water discharging angle A2 of the water outlet spout 2 of Embodiment 3. Referring to FIGS. 26, A1 and A2 are respectively less than 90°. Referring to FIG. 27, A1 is less than 90°, and A2 is equal to 90°. Referring to FIG. 28, A1 is less than 90°, and A2 is greater than 90°. Referring to FIG. 29, A1 is equal to 90°, and A2 is greater than 90°. Referring to FIGS. 30, A1 and A2 are respectively equal to 90°. Referring to FIG. 31, A1 is equal to 90°, and A2 is greater than 90°. Referring to FIG. 32, A1 is greater than 90°, and A2 is less than 90°. Referring to FIG. 33, A1 is greater than 90°, and A2 is equal to 90°. Referring to FIG. 34, A1 is greater than 90° and A2 is greater than 90°.

Embodiment 4

In this embodiment, the camera lens 3 is arranged in the water outlet opening of the water outlet spout 2. A positional relationship between the water outlet spout 2 and the camera lens 3 in this embodiment is the same as that in Embodiment 1 and will not be further described here.

The aforementioned embodiments are merely some embodiments of the present disclosure, and the scope of the disclosure is not limited thereto. Thus, it is intended that the present disclosure cover any modifications and variations of the presently presented embodiments provided they are made without departing from the appended claims and the specification of the present disclosure by those skilled in the art.

What is claimed is:

1. A water flosser with an image system, comprising:
a body,
a water outlet spout, and
an image system, wherein:
the water outlet spout and a camera lens of the image system are disposed on the body, and
an area covered by ejected water ejected from the water outlet spout at least partially coincides with an image area of the image system.

2. The water flosser with the image system according to claim 1, wherein a connection position between the image system and the body is disposed on a side of the water outlet spout facing the ejected water.

3. The water flosser with the image system according to claim 2, wherein a lens surface of the image system is lower than a water outlet surface of the water outlet spout.

4. The water flosser with the image system according to claim 1, wherein a connection position between the image system and the body is disposed on a side of the water outlet spout opposite to the ejected water.

5. The water flosser with the image system according to claim 4, wherein a lens surface of the image system is higher than a water outlet surface of the water outlet spout.

6. The water flosser with the image system according to claim 1, wherein a lens surface of the image system is disposed on a side of a water outlet opening of the water outlet spout.

7. The water flosser with the image system according to claim 1, wherein the image system is disposed in a water outlet opening of the water outlet spout.

8. The water flosser with the image system according to claim 1, wherein the area covered by the ejected water ejected from the water outlet spout always appears in the image area of the image system.

9. The water flosser with the image system according to claim 1, wherein the water outlet spout and the camera lens are respectively detachably connected to the body.

10. The water flosser with the image system according to claim 1, wherein the camera lens and the body define a non-detachable connection.

11. The water flosser with the image system according to claim 1, wherein one or more control switches are disposed on the body.

12. The water flosser with the image system according to claim 11, wherein:
the one or more control switches comprise at least one switch configured to control the water outlet spout to discharge water or to stop discharging water, or
the one or more control switches are configured to control the image system to be switched on or to be switched off.

13. The water flosser with the image system according to claim 12, wherein:
the one or more control switches comprise an image switch, and
after the image system is switched on, the image switch is pressed to photograph a current image area of the image system.

14. The water flosser with the image system according to claim 13, wherein a water flosser control switch of the one or more control switches is repeatedly pressed to change a water outlet gear position of the water outlet spout.

15. The water flosser with the image system according to claim 1, wherein an image processing portion of the image system is disposed in the body.

16. The water flosser with the image system according to claim 11, wherein a water flosser control switch of the one or more control switches and a lighting switch of the one or more control switches are independent from each other.

17. The water flosser with the image system according to claim 1, wherein the body comprises a water tank, and a bottom portion of the body comprises a cover configured to open or close the water tank.

18. The water flosser with the image system according to claim 1, wherein the body comprises a cavity for accommodating the camera lens and the water outlet spout.

19. The water flosser with the image system according to claim 1, wherein:
- a lens surface of the camera lens faces the water outlet spout, and
- a water outlet opening of the water outlet spout is positioned in the image area of the camera lens.

\* \* \* \* \*